United States Patent
Namose (10) Patent No.: US 7,067,813 B2
(45) Date of Patent: Jun. 27, 2006

(54) INFRARED ABSORPTION MEASUREMENT METHOD, INFRARED ABSORPTION MEASUREMENT DEVICE, AND METHOD OF MANUFACTURING SEMICONDUCTOR DEVICE

(75) Inventor: Isamu Namose, Suwa (JP)

(73) Assignee: Seiko Epson Corporation, Tokyo (JP)

( * ) Notice: Subject to any disclaimer, the term of this patent is extended or adjusted under 35 U.S.C. 154(b) by 358 days.

(21) Appl. No.: 10/756,316

(22) Filed: Jan. 14, 2004

(65) Prior Publication Data

US 2004/0188621 A1    Sep. 30, 2004

(30) Foreign Application Priority Data

Jan. 20, 2003   (JP) .............................. 2003-011124

(51) Int. Cl.
   *G01N 21/61* (2006.01)
(52) U.S. Cl. ................................. 250/343; 250/339.13
(58) Field of Classification Search ................ 250/343, 250/339.13, 339.1, 338.5
   See application file for complete search history.

(56) References Cited

U.S. PATENT DOCUMENTS

| | | | | |
|---|---|---|---|---|
| 3,869,613 A | * | 3/1975 | Link et al. ................. | 250/343 |
| 3,904,880 A | * | 9/1975 | Benz et al. ................. | 250/343 |
| 4,110,618 A | * | 8/1978 | Schuman .................... | 250/343 |
| 5,449,912 A | * | 9/1995 | Mayer ........................ | 250/343 |
| 5,473,161 A | * | 12/1995 | Nix et al. ................... | 250/343 |
| 5,625,189 A | * | 4/1997 | McCaul et al. ............. | 250/343 |
| 5,703,365 A | * | 12/1997 | Ishihara et al. ......... | 250/339.13 |
| 6,254,828 B1 | * | 7/2001 | LaCount ....................... | 422/78 |
| 2004/0164237 A1 | * | 8/2004 | Jones et al. .............. | 250/269.1 |
| 2004/0200963 A1 | * | 10/2004 | Namose ................ | 250/339.13 |

FOREIGN PATENT DOCUMENTS

| | | |
|---|---|---|
| JP | A 5-249040 | 9/1993 |
| JP | A-05-332921 | 12/1993 |
| JP | A 6-281578 | 10/1994 |
| JP | A 10-221253 | 8/1998 |
| JP | A-11-258156 | 9/1999 |
| JP | A-2002-082049 | 3/2002 |
| WO | WO 95/26497 A1 | 10/1995 |

* cited by examiner

*Primary Examiner*—Albeert Gagliardi
(74) *Attorney, Agent, or Firm*—Oliff & Berridge, PLC (57) ABSTRACT

An infrared absorption measurement method including: (a) measuring infrared absorption of a target component in a sample gas while decompressing the sample gas so that an absorption area in a peak region of the target component in the infrared absorption shown in a graph is within a predetermined range, the graph showing the relationship between the wave number and absorbance of the sample gas; and (b) calculating the concentration of the target component in the sample gas based on the absorption area and pressure of the decompressed sample gas.

11 Claims, 8 Drawing Sheets

INFRARED ABSORPTION MEASUREMENT METHOD, INFRARED ABSORPTION MEASUREMENT DEVICE, AND METHOD OF MANUFACTURING SEMICONDUCTOR DEVICE

Japanese Patent Application No. 2003-11124, filed on Jan. 20, 2003 is hereby incorporated by reference in its entirety.

BACKGROUND OF THE INVENTION

The present invention relates to an inexpensive and highly accurate infrared absorption measurement method and an inexpensive and highly accurate infrared absorption measurement device.

The present invention also relates to a method of manufacturing a semiconductor device using the infrared absorption measurement method.

In the case of measuring the infrared absorption of a sample (see Japanese Patent Application Laid-open No. 2002-82049, for example), a cell having a suitable cell length is appropriately selected depending on the concentration of the sample. In this case, since the absorbance is saturated if the concentration of the sample is too high, a cell having a greater cell length must be used. Specifically, a plurality of cells must be provided corresponding to the concentration of the sample. However, a cell used for infrared absorption measurement is expensive. Therefore, since a considerable cost is necessary to provide a plurality of cells, the measurement cost is increased.

BRIEF SUMMARY OF THE INVENTION

The present invention may provide an inexpensive and highly accurate infrared absorption measurement method and an inexpensive and highly accurate infrared absorption measurement device.

The present invention may also provide a method of manufacturing a semiconductor device using the infrared absorption measurement method.

According to one aspect of the present invention, there is provided an infrared absorption measurement method comprising:

(a) measuring infrared absorption of a target component in a sample gas while decompressing the sample gas so that an absorption area in a peak region of the target component in the infrared absorption shown in a graph is within a predetermined range, the graph showing the relationship between the wave number and absorbance of the sample gas; and (b) calculating the concentration of the target component in the sample gas based on the absorption area and pressure of the decompressed sample gas.

According to another aspect of the present invention, there is provided a method of manufacturing a semiconductor device, comprising:

calculating the concentration of the target component in the sample gas by using the infrared absorption measurement method as defined in claim 1, wherein the target component is included in a gas discharged from a semiconductor manufacturing device.

According to a further aspect of the present invention, there is provided an infrared absorption measurement device comprising:

a pump which decompresses a sample gas including a target component;

an infrared absorption analysis device which measures infrared absorption of the target component in the sample gas decompressed by the pump; and a feedback mechanism which adjusts the pressure of the sample gas so that an absorption area in a peak region of the target component in the infrared absorption shown in a graph is within a predetermined range, the graph showing the relationship between the wave number and absorbance of the sample gas.

DETAILED DESCRIPTION OF THE EMBODIMENT

According to one embodiment of the present invention, there is provided an infrared absorption measurement method comprising:

(a) measuring infrared absorption of a target component in a sample gas while decompressing the sample gas so that an absorption area in a peak region of the target component in the infrared absorption shown in a graph is within a predetermined range, the graph showing the relationship between the wave number and absorbance of the sample gas; and (b) calculating the concentration of the target component in the sample gas based on the absorption area and pressure of the decompressed sample gas.

The infrared absorption measurement method has no need to change a cell used for infrared absorption measurement depending on the concentration of the target component, since the sample gas is decompressed in the measurement of the infrared absorption so that the absorption area in the peak region of the target component in the infrared absorption is within the predetermined range. This enables the cost of the measurement to be reduced. As a result, the infrared absorption can be measured at the reduced cost with high accuracy.

Moreover, by introducing the decompressed sample gas for the measurement of the infrared absorption, the time period of necessary for the sample gas to be introduced into a cell and discharged from the cell can be reduced in comparison with the case of measuring the sample gas under normal pressure. Therefore, the time period necessary for the measurement can be reduced, whereby efficiency of the measurement can be improved. Note that the "normal pressure" used herein refers to atmospheric pressure.

The infrared absorption measurement method according to the present invention may have the following features.

A temporary concentration $M_1$ corresponding to the absorption area may be calculated in the step (b) by referring a calibration curve which represents the relationship between the concentration and absorption area of a reference gas including the target component; and when the pressure of the reference gas is $P_1$ and the pressure of the decompressed sample gas is $P_2$, a concentration $M_2$ of the sample gas is obtained by: $M_2 = M_1 P_1 / P_2$.

The calibration curve represents the relationship between the absorption area of the target component and the concentration of the target component of the reference gas under predetermined pressure.

A temporary concentration $M_1$ (see the above equation) can be set within a range which enables to obtain an accurate value of the concentration $M_2$ of the target component, by adjusting the pressure $P_2$ of the decompressed sample gas. The concentration $M_2$ of the target component thus can be accurately measured from the above equation by utilizing the calibration curve.

The sample gas may be decompressed in the step (a) so that the absorption area has a predetermined value. This enables to simply calculate the concentration of the target component from the pressure of the sample gas when the absorption area has the predetermined value.

An infrared absorption region of the target component shown in the above graph may include a main peak region and a sub-peak region; and the peak region may be the main peak region. In this case, the concentration of the target component can be accurately measured by decompressing the sample gas without changing a cell used for infrared absorption measurement, even if the concentration of the target component is extremely high.

The target component may be included in a gas discharged from a semiconductor manufacturing device.

According to one embodiment of the present invention, there is provided a method of manufacturing a semiconductor device, comprising:

calculating the concentration of the target component in the sample gas by using the infrared absorption measurement method as defined in claim 1, wherein the target component is included in a gas discharged from a semiconductor manufacturing device.

In this method of manufacturing a semiconductor device, the infrared absorption is measured for the decompressed gas in a cell used for infrared absorption measurement, so the time in which the sample gas stays in the cell can be reduced in comparison with the case of measuring the sample gas under normal pressure. This prevents solid products included in the sample gas and discharged from a semiconductor manufacturing device together with a discharged gas from adhering to the cell.

According to one embodiment of the present invention, there is provided an infrared absorption measurement device comprising:

a pump which decompresses a sample gas including a target component;

an infrared absorption analysis device which measures infrared absorption of the target component in the sample gas decompressed by the pump; and a feedback mechanism which adjusts the pressure of the sample gas so that an absorption area in a peak region of the target component in the infrared absorption shown in a graph is within a predetermined range, the graph showing the relationship between the wave number and absorbance of the sample gas.

This infrared absorption measurement device has effects similar to the effects of the above infrared absorption measurement method.

In this case, the feedback mechanism may adjust the pressure of the sample gas so that the absorption area has a predetermined value.

Moreover, the infrared absorption analysis device may include an analysis section which calculates the absorption area and transmits information on the absorption area to the feedback mechanism; and the feedback mechanism may adjust the pressure of the sample gas based on the transmitted information on the absorption area.

This infrared absorption measurement device may further comprise a concentration calculation section which calculates the concentration of the target component in the sample gas based on the information on the absorption area and information on the pressure of the sample gas.

An infrared absorption region of the target component shown in the above graph may include a main peak region and a sub-peak region; and the peak region may be the main peak region.

These embodiments of the present invention will be described below with reference to the drawings.

1. First Embodiment 1.1. Infrared Absorption Measurement Device

Figure 1:
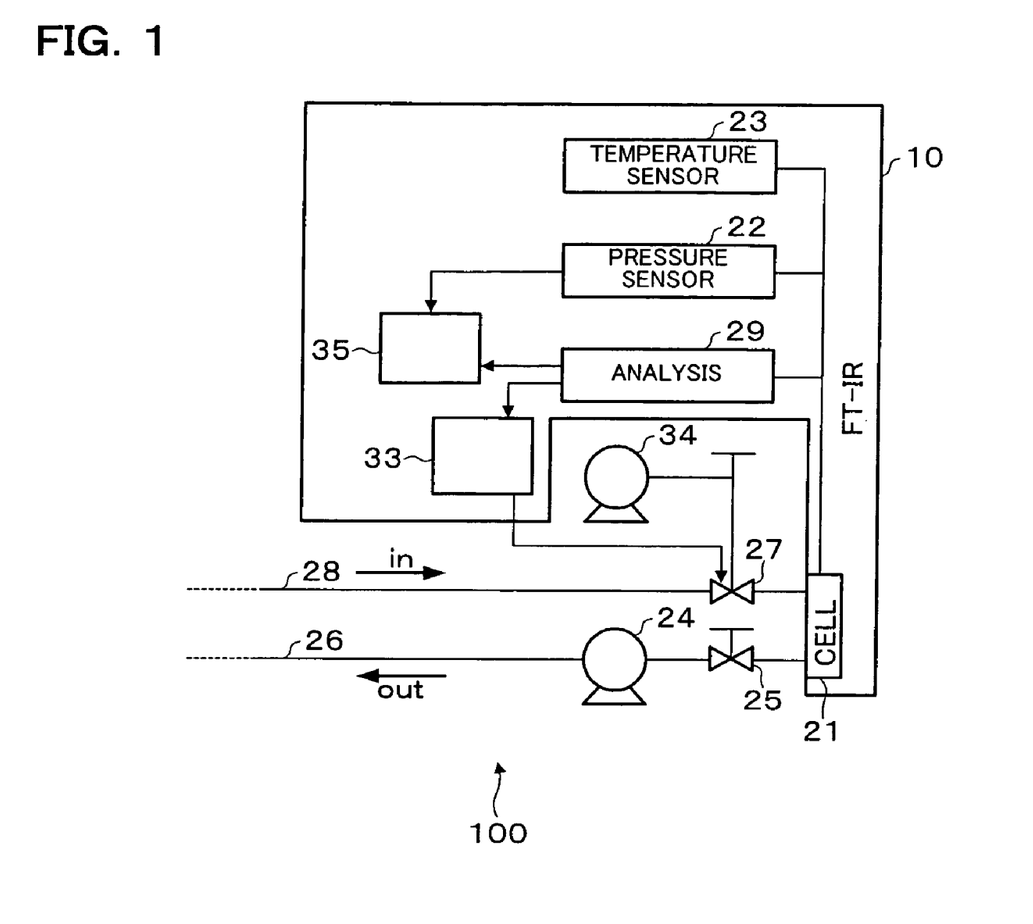
FIG. 1 is a diagram schematically showing an infrared absorption measurement device according to a first embodiment of the present invention.

FIG. 1 is a diagram schematically showing an infrared absorption measurement device 100 according to this embodiment of the present invention.

In the infrared absorption measurement device 100 in this embodiment, a sample gas including a target component is introduced into an infrared absorption analysis device 10 through a gas inlet line 28, and infrared absorption of the target component is measured by using the infrared absorption analysis device 10. Specifically, the target component included in the sample gas is the target of infrared absorption measurement.

The sample gas includes at least one type of target component. In this embodiment, the case where the sample gas includes one type of target component ($CHF_3$) is described below as an example.

As shown in FIG. 1, the infrared absorption measurement device 100 includes a pump 34 for decompressing the sample gas. The pump 34 is provided in the middle of the gas inlet line 28 through a valve 27. A needle valve may be used as the valve 27, for example. The pressure of the sample gas may be adjusted by using the valve 27. The sample gas introduced into the gas inlet line 28 is decompressed by using the pump 34, and introduced into the infrared absorption analysis device 10. In the infrared absorption analysis device 10, infrared absorption is measured in a state in which the sample gas is decompressed.

After the measurement, the sample gas is discharged from the infrared absorption analysis device 10 through a discharge line 26.

The infrared absorption analysis device 10 includes a cell 21 used for infrared absorption measurement, a temperature sensor 23 which detects the temperature in the cell 21, a pressure sensor 22 which detects the pressure of the sample gas in the cell 21, and an analysis section 29 which analyzes the measured infrared absorption. The information on the pressure of the sample gas detected by the pressure sensor 22 is transmitted to a concentration calculation section 35 described later.

The analysis section 29 calculates the absorption area of the peak region which indicates the target component in the measured infrared absorption. The wavelength band including the peak region of the target component is set in advance in the analysis section 29. Therefore, if the infrared absorption is obtained, the analysis section 29 calculates the absorption area of the peak region which exists in the wavelength band. The information on the absorption area calculated by the analysis section 29 is transmitted to the concentration calculation section 35 described later.

The infrared absorption measurement device 100 in this embodiment further includes a feedback mechanism section 33. The feedback mechanism section 33 has a function of adjusting the pressure of the sample gas based on the information on the absorption area of the peak region of the target component analyzed by the analysis section 29.

In more detail, the information on the absorption area of the peak region is transmitted to the feedback mechanism section 33 from the analysis section 29, and the information on the pressure of the sample gas in the cell 21 is transmitted to the feedback mechanism section 33 from the pressure sensor 22. The feedback mechanism section 33 transmits a signal for controlling the valve 27 to the valve 27 based on the above information so that the absorption area is within a predetermined range. This allows opening and closing of the valve 27 to be adjusted, whereby the pressure of the sample gas in the cell 21 is adjusted.

The infrared absorption measurement device 100 in this embodiment further includes the concentration calculation section 35. The concentration calculation section 35 calculates the concentration of the target component in the sample gas based on the information on the absorption area transmitted from the analysis section 29 and the information on the pressure of the sample gas transmitted from the pressure sensor 22.

The feedback mechanism section 33 and the concentration calculation section 35 may be software included in the infrared absorption analysis device 10, for example.

FIG. 1 illustrates the case where a Fourier transform infrared spectrometer (FT-IR) is used as the infrared absorption analysis device 10. However, the type of the infrared absorption analysis device 10 is not limited. In the following description, measurement data is the experimental results obtained by using IGA2000 manufactured by MIDAC Corporation as the FT-IR. In the measurement, a cell having a length of 1 cm was used.

1.2. Infrared Absorption Measurement Method

The infrared absorption measurement method using the infrared absorption measurement device 100 shown in FIG. 1 is described below with reference to a flowchart shown in FIG. 3.

In the infrared absorption measurement device 100, the infrared absorption of the target component in the sample gas is measured in a state in which the sample gas is decompressed so that the absorption area of the peak region which indicates the target component ($CHF_3$) in the infrared absorption is within a predetermined range. In the case where the absorption area exists within the predetermined range, the concentration of the target component in the sample gas is calculated based on the absorption area and the pressure of the sample gas at which the absorption area is obtained. The infrared absorption measurement method is described below in detail with reference to FIG. 3.

1.2.1. Measurement of Infrared Absorption and Calculation of Absorption Area

In the infrared absorption measurement device 100, infrared absorption of the target component is measured by using the infrared absorption analysis device 10 in a state in which the sample gas including the target component is decompressed. In more detail, the sample gas decompressed by using the pump 34 is introduced into the cell 21 in the infrared absorption analysis device 10, and infrared absorption of the target component is measured by using the cell 21.

The absorption area of the peak region which indicates the target component is calculated from the measured infrared absorption by using the analysis section 29 (step S1). In more detail, the absorption area of the peak region which indicates the target component is calculated by using the analysis section 29 from the infrared absorption spectrum of the target component measured by using the cell 21.

In the case where the absorption area is within the predetermined range, the pressure $P_2$ of the sample gas in the cell 21 is measured (steps S2 and S6). In more detail, the pressure $P_2$ of the sample gas is detected by the pressure sensor 22. After the measurement, the sample gas is discharged from the cell 21, and discharged to the outside through the discharge line 26.

In the case where the absorption area is not within the predetermined range, such as the case where the absorption area exceeds the predetermined range, a signal which informs to that effect is transmitted to the feedback mechanism section 33 from the analysis section 29 (steps S2 and S3). As a result, a signal for decreasing the pressure of the sample gas in the cell 21 is transmitted to the valve 27 from the feedback mechanism section 33 (step S5). In the case where the absorption area is smaller than the predetermined range, a signal which informs to that effect is transmitted to the feedback mechanism section 33 from the analysis section 29 (steps S3). As a result, a signal for increasing the pressure of the sample gas in the cell 21 is transmitted to the valve 27 from the feedback mechanism section 33 (step S4). The absorption area can be set within the predetermined range by repeating the processing in the steps S1 to S5 shown in FIG. 3. In the case where the absorption area is within the predetermined range, the pressure of the sample gas is measured (step S6).

1.2.2. Concentration of Target Component

The concentration of the target component in the sample gas is calculated from the obtained absorption area and pressure of the sample gas (step S7). The concentration of the target component is calculated by the concentration calculation section 35. Specifically, the concentration calculation section 35 calculates the concentration of the target component in the sample gas based on the absorption area information transmitted from the analysis section 29 and the pressure information of the sample gas transmitted from the pressure sensor 22. The measurement procedure of the concentration of the target component in the concentration calculation section 35 is described below.

The temporary concentration $M_1$ corresponding to the absorption area is calculated by referring to a calibration curve. The calibration curve shows the relationship between the concentration and the absorption area of the target component, and is created by using the following method. A known calibration curve may be used instead of creating the calibration curve.

I. Calibration Curve

The calibration curve is obtained by calculating the absorption area by measuring the infrared absorption of a gas including a known concentration of the target component, calculating the absorption area while changing the concentration of the target component, and plotting absorption area versus concentration. In the measurement of the concentration of the target component for creating the calibration curve, the pressure of the gas is made constant. The pressure of the gas is referred to as $P_1$.

In the infrared absorption, the concentration of the target component in the gas to be measured is proportional to the absorption area of the target component at the concentration under conditions where the pressure is constant. Therefore, the calibration curve is obtained by plotting the absorption area versus the concentration of the target component under conditions where the pressure is constant.

Figure 5:
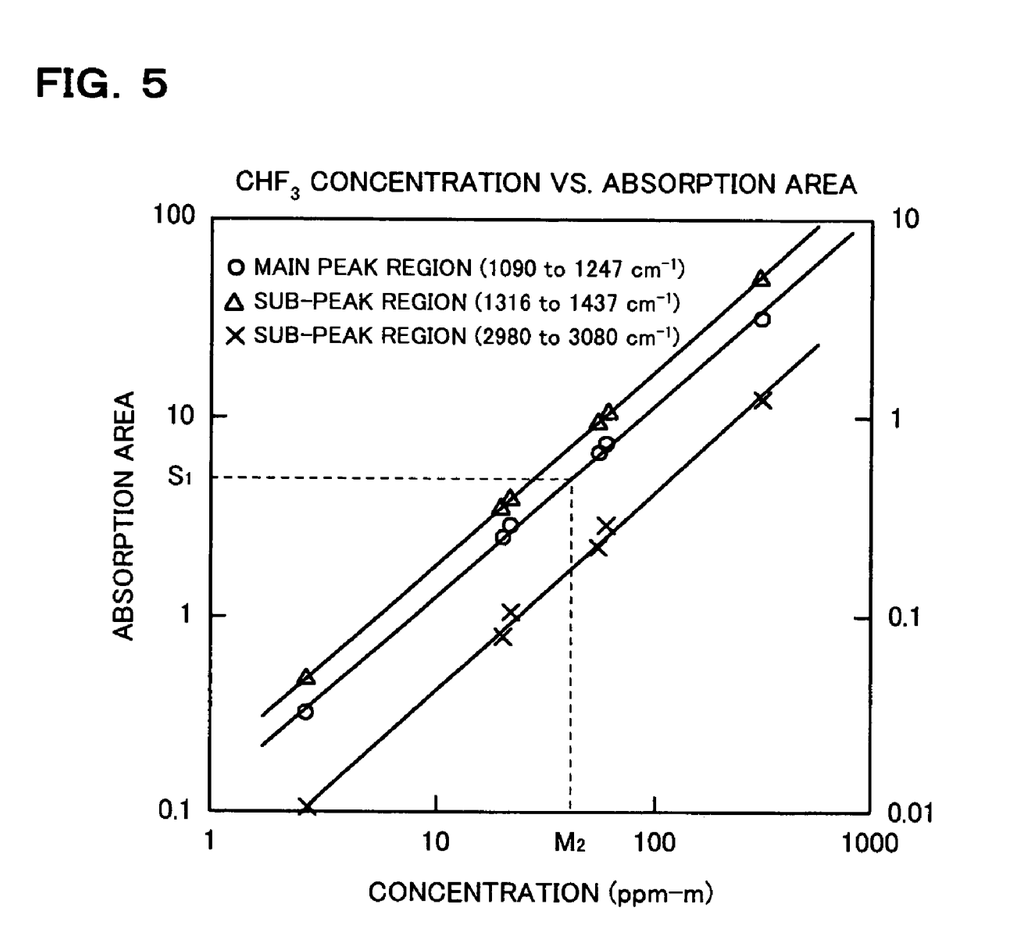
FIG. 5 is a graph showing a calibration curve which represents the relationship between the concentration and absorption area of $CHF_3$ in a main peak region and a sub-peak region in another graph showing the relationship between the wave number and absorbance of $CHF_3$.

As an example, the case where the target component is $CHF_3$ is described below. FIG. 5 shows a calibration curve based on $CHF_3$. This calibration curve shows the absorption area versus the concentration of the target component ($CHF_3$). In FIG. 5, the vertical axis indicates the absorption area and the horizontal axis indicates the $CHF_3$ concentration.

$CHF_3$ has a main peak region (1090 to 1247 $cm^{-1}$) and two sub-peak regions (1316 to 1437 $cm^{-1}$ and 2980 to 3080 $cm^{-1}$) in the infrared absorption region. Therefore, in the case where the target component is $CHF_3$, calibration curves can be created for each of the main peak region and the sub-peak regions. FIG. 5 shows the calibration curve based on the main peak region and two calibration curves based on two sub-peak regions.

In this embodiment, the case where the $CHF_3$ concentration is calculated by calculating the absorption area based on the main peak region is described. In FIG. 5, the vertical axis (absorption area) of the calibration curve based on the main peak region is indicated by a value using the scale on the left of the graph, and the vertical axis of the calibration curve based on the sub-peak region is indicated by a value using the scale on the right. The calibration curve shown in FIG. 5 is based on measurement results obtained by measuring infrared absorption in a state in which the pressure of the gas including the target component ($CHF_3$) is normal pressure.

II. Calculation of Concentration

As shown in FIG. 5, in the case where the target component is $CHF_3$, the absorption area $S_1$ is obtained, for example. In the calibration curve based on the main peak region shown in FIG. 5, the concentration (temporary concentration) of $CHF_3$ in the gas is $M_1$.

In the case where the pressure of the gas is constant, the absorption area of the target component is proportional to the concentration of the target component. In the case where the absorption area of the target component is constant, the concentration of the target component is inversely proportional to the pressure of the target component.

If the pressure of the gas including the target component used to create the calibration curve during infrared absorption measurement is $P_1$, and the pressure of the sample gas during decompression is $P_2$, the concentration $M_2$ of the target component in the sample gas is expressed by the following equation (1).

$$M_2 = M_1 P_1 / P_2 \qquad (1)$$

Therefore, the concentration $M_2$ of the target component in the sample gas is obtained based on the equation (1) by measuring the temporary concentration $M_1$ and the pressures $P_1$ and $P_2$.

1.3. Effects

The effects in this embodiment are described below. A conventional infrared absorption measurement method is described in order to compare its effects with the effects in this embodiment.

1.3.1. Conventional Infrared Absorption Measurement Method

In a conventional infrared absorption measurement, a cell having a suitable cell length must be selected corresponding to the concentration of the target component in the gas to be measured. Generally, a cell having a small cell length is used when the concentration of the target component is high, and a cell having a large cell length is used when the concentration of the target component is low.

Figure 6:
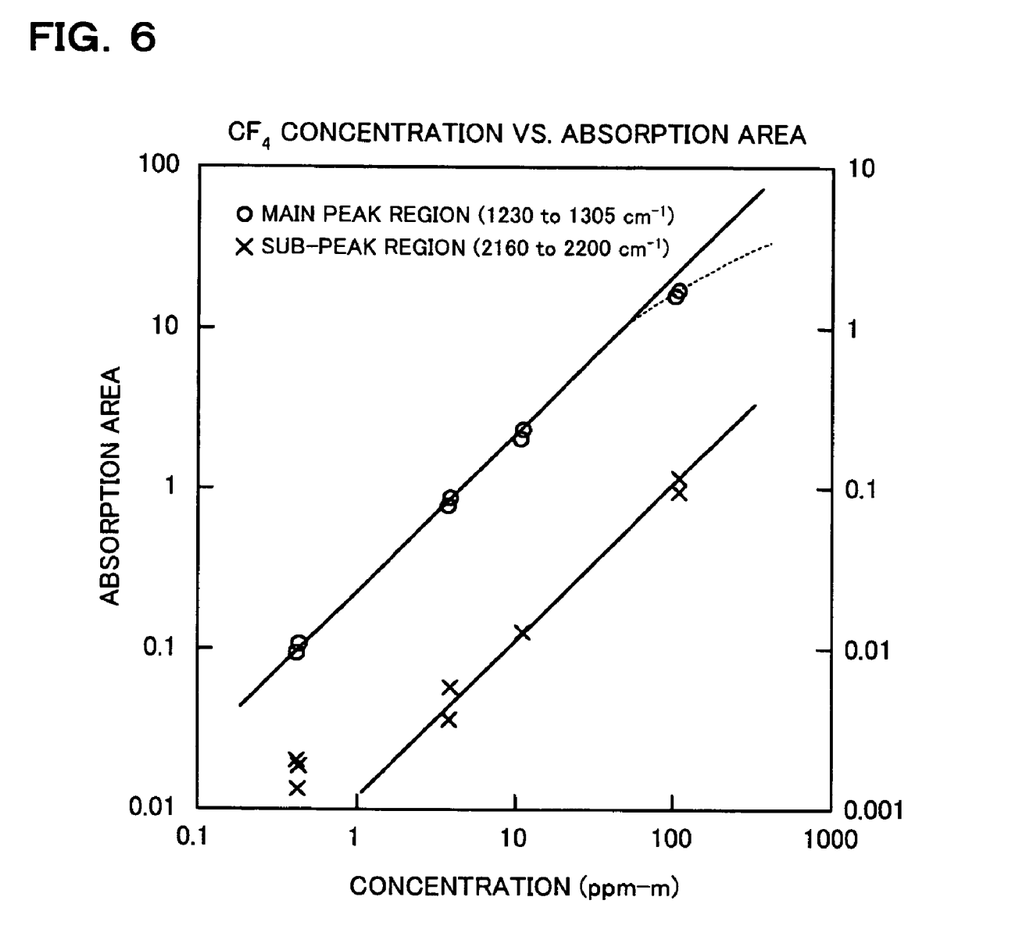
FIG. 6 is a graph showing a calibration curve which represents the relationship between the concentration and absorption area of $CF_4$ in a main peak region and a sub-peak region in another graph showing the relationship between the wave number and absorbance of $CF_4$.

There may be a case where an accurate calibration curve cannot be obtained depending on the type or concentration of the target component. As an example, the case where the target component is $CF_4$ is described below. FIG. 6 shows a calibration curve based on $CF_4$. In FIG. 6, the vertical axis (absorption area) of the calibration curve based on the main peak region is indicated by a value using the scale on the left of the graph, and the vertical axis of the calibration curve based on the sub-peak region is indicated by a value using the scale on the right. The calibration curve shown in FIG. 6 is based on the measurement results obtained by measuring infrared absorption in a state in which the pressure of the gas including the target component ($CF_4$) is approximately equal to atmospheric pressure.

As shown in FIG. 6, in the case of using $CF_4$ as the target component, linearity of the calibration curve based on the main peak region is lost in the region in which the concentration of the target component is high (see dotted line in FIG. 6). The reasons therefor are described below.

Figure 7:
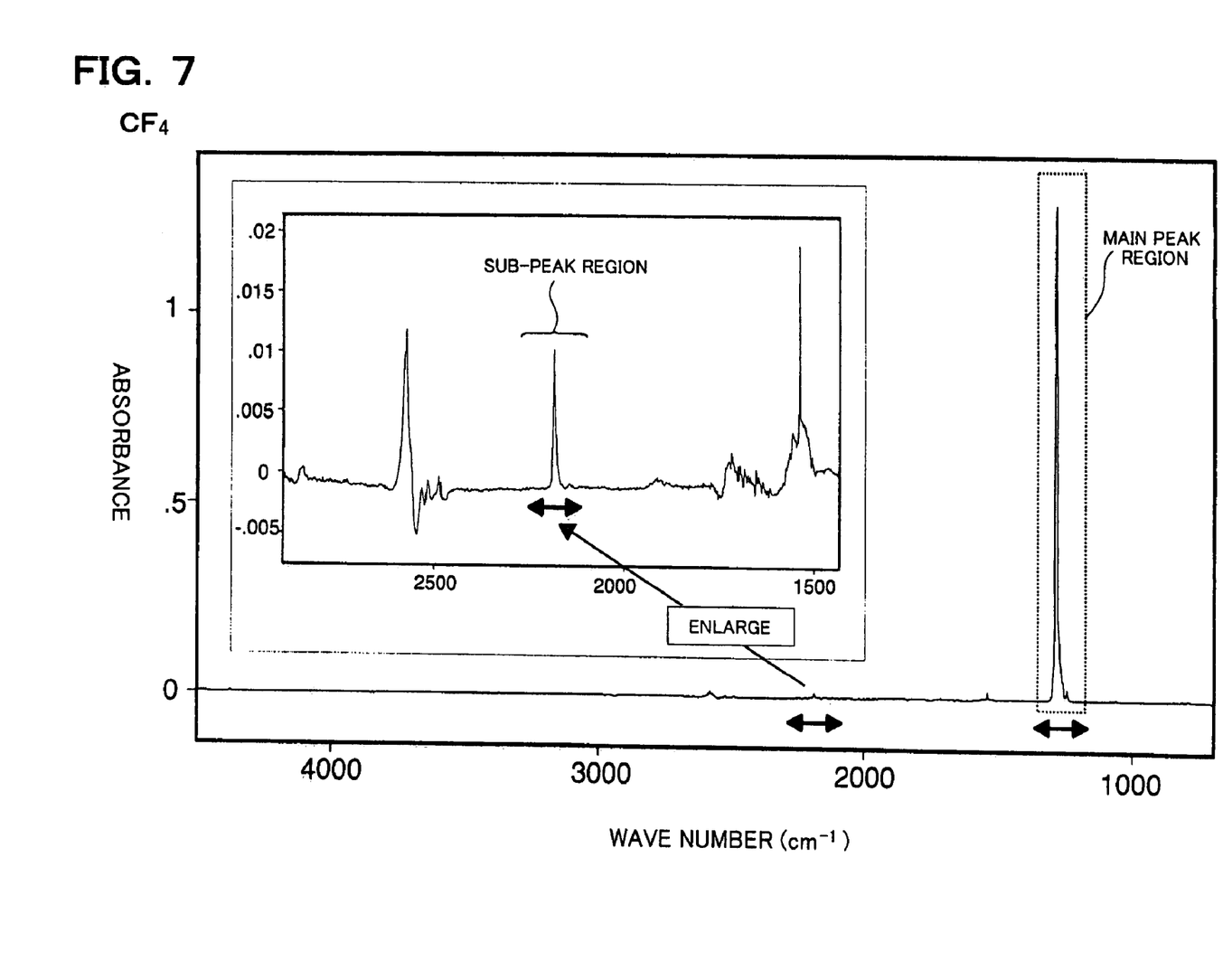
FIG. 7 shows a main peak region and a sub-peak region in a graph showing the relationship between the wave number and absorbance of $CF_4$.
Figure 8A:
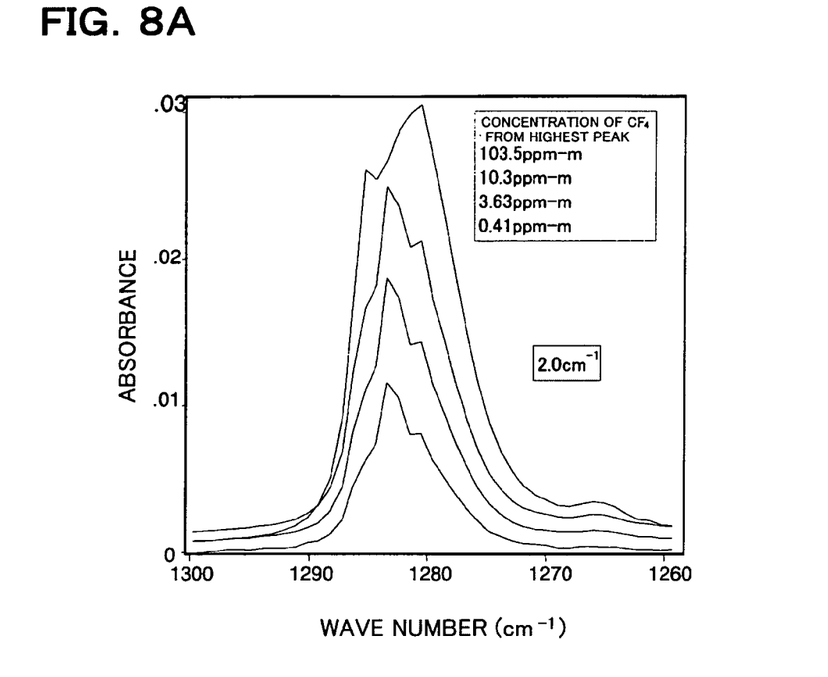
FIGS. 8A and 8B are enlarged views of a main peak region in another graph showing the relationship between the wave number and absorbance of $CF_4$.
Figure 8B:
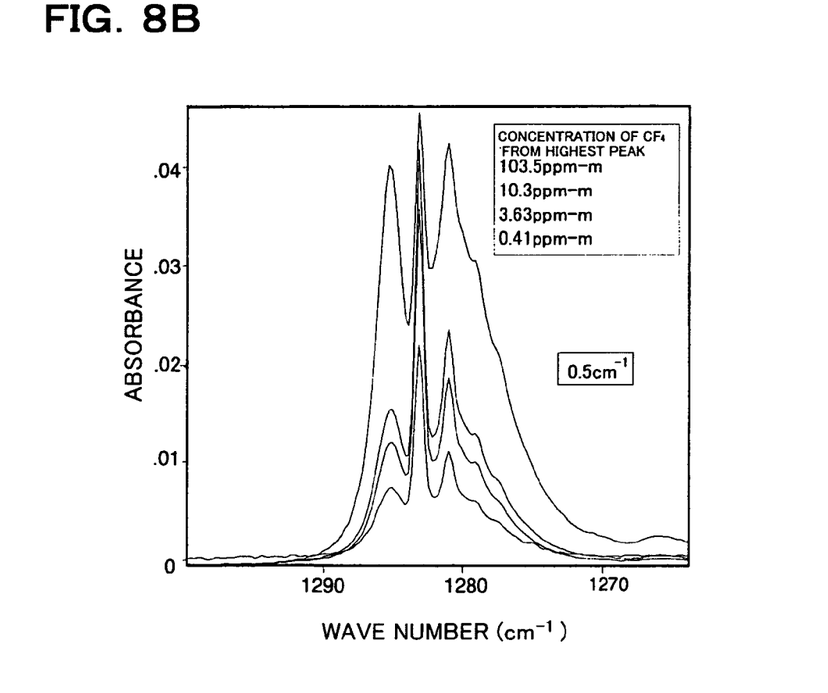

As shown in FIG. 6, $CF_4$ has a main peak region (1230 to 1305 $cm^{-1}$) and a sub-peak region (2160 to 2200 $cm^{-1}$) in the infrared absorption region. FIG. 7 shows the infrared absorption spectrum of $CF_4$ and an enlarged view of the sub-peak region. FIGS. 8A and 8B show enlarged views of the main peak region of $CF_4$. FIG. 8B shows the results measured at a resolving power higher than that of FIG. 8A.

In FIG. 7, the peak which exists in the main peak region of $CF_4$ seems to be a single peak. However, as shown in the enlarged views of FIGS. 8A and 8B, a plurality of peaks exist in the main peak region of $CF_4$. Therefore, in the case of creating a calibration curve based on the main peak region of $CF_4$, an accurate calibration curve is not obtained if the calibration curve is created while ignoring the existence of the peaks shown in FIG. 8B.

FIGS. 8A and 8B show infrared absorption waveforms in the main peak region (1230 to 1305 $cm^{-1}$) in the case where $CF_4$ has different concentrations. In more detail, FIGS. 8A and 8B show infrared absorption waveforms in the case where the $CF_4$ concentration is 103.5 ppm-m, 10.3 ppm-m, 3.63 ppm-m, and 0.41 ppm-m in the order from the highest peak. In FIGS. 8A and 8B, the area (absorption area) enclosed by the waveform and the horizontal axis (wave number) is proportional to the $CF_4$ concentration. Therefore, in the case of calculating the concentration of $CF_4$ included in the sample gas, the absorption area is calculated by referring to FIGS. 8A and 8B after measuring infrared absorption, and the $CF_4$ concentration is calculated from the absorption area by referring to the calibration curve shown in FIG. 6.

In the main peak region of $CF_4$, the height of the peak included in the waveform is increased as the $CF_4$ concentration is increased in the order of 0.41 ppm-m, 3.63 ppm-m, and 10.3 ppm-m, as shown in FIG. 8B. However, even if the $CF_4$ concentration is further increased to 103.5 ppm-m, the height of the highest peak is not increased in proportion to the concentration, and is saturated at a certain absorbance. Specifically, in the case of calculating the concentration of $CF_4$ included in the sample gas by using the calibration curve based on the main peak region, the absorption area is not proportional to the $CF_4$ concentration in the region in which the $CF_4$ concentration is high, as shown in FIG. 6. Therefore, an accurate concentration may not be calculated based on the absorption area.

For the reasons described above, reliability of the calibration curve based on the main peak region of $CF_4$ is decreased in the high concentration region. The calibration curve based on the sub-peak region of $CF_4$ may be used in the region in which the $CF_4$ concentration is high. However, the calibration curve based on the sub-peak region excels in linearity in the region in which the $CF_4$ concentration is high, but has poor linearity in the region in which the $CF_4$ concentration is low, as shown in FIG. 6. As shown in FIG. 7, the height of the peak of $CF_4$ which exists in the sub-peak region is very small in comparison with the height of the peak which exists in the main peak region. Therefore, it is difficult to accurately determine the peak of $CF_4$ in the region in which the $CF_4$ concentration is low due to the influence of noise, whereby the amount of error in the $CF_4$ concentration is increased. Therefore, reliability of the resulting $CF_4$ concentration may be decreased if the calibration curve based on the sub-peak region is used in the region in which the $CF_4$ concentration is low.

1.3.2. Effects

According to the infrared absorption measurement method in this embodiment, the infrared absorption of the target component in the sample gas is measured in a state in which the sample gas is decompressed so that the absorption area of the peak region which indicates the target component in the infrared absorption is within the predetermined range. The concentration of the target component in the sample gas is calculated from the absorption area and the pressure of the sample gas during decompression. Specifically, the temporary concentration Ml corresponding to the absorption area is calculated from the absorption area and the pressure of the sample gas during decompression by referring to the calibration curve of the target component. If the pressure of the gas including the target component used to create the calibration curve during infrared absorption measurement is $P_1$, and the pressure of the sample gas during decompression is $P_2$, the concentration $M_2$ of the sample gas is calculated by using the above equation (1).

As described above, according to the infrared absorption measurement method in this embodiment, the absorption area can be set within the predetermined range by adjusting the pressure of the sample gas corresponding to the concentration of the target component in the sample gas. Therefore, the absorption area can be measured without replacing the cell. This enables cost necessary for the measurement to be reduced. As a result, infrared absorption can be measured at low cost with high accuracy.

According to the infrared absorption measurement method in this embodiment, the temporary concentration $M_1$ (see equation 1) can be set within the concentration range which allows the concentration $M_2$ of the target component to be accurately obtained by adjusting the pressure $P_2$ of the sample gas during decompression while measuring the infrared absorption of the target component in the sample gas. This enables the concentration $M_2$ of the target component to be accurately measured based on the equation (1) by utilizing the calibration curve.

In the case where the target component is $CF_4$, since linearity of the calibration curve based on the main peak region is poor in the high concentration region, it is difficult to obtain an accurate concentration in the high concentration region. In this case, if the calibration curve based on the sub-peak region is used, reliability of the calibration curve is decreased due to the influence of noise, whereby an accurate concentration cannot be obtained. On the contrary, according to the infrared absorption measurement method in this embodiment, the temporary concentration $M_1$ (see equation 1) can be set within the concentration range which allows accurate measurement to be performed in the calibration curve based on the main peak region by adjusting the pressure $P_2$ of the sample gas during decompression. This enables the concentration $M_2$ of the target component to be accurately measured based on the equation (1) by utilizing the calibration curve based on the main peak region.

Moreover, the period of time necessary for the sample gas to be introduced into the cell 21 and discharged from the cell 21 can be reduced in comparison with the case of measuring the sample gas under normal pressure by measuring the infrared absorption in the cell 21 while introducing the sample gas in a decompressed state. Therefore, the period of time necessary for the measurement can be reduced, whereby efficiency of the measurement can be increased.

This embodiment illustrates the case where the concentration of $CF_4$ as the target component is calculated by using the calibration curve based on the main peak region. However, use of the calibration curve based on either the main peak region or the sub-peak region is determined based on the type of the target component or other components included in the sample gas. This also applies to embodiments described later.

1.4. Modification

Figure 3:
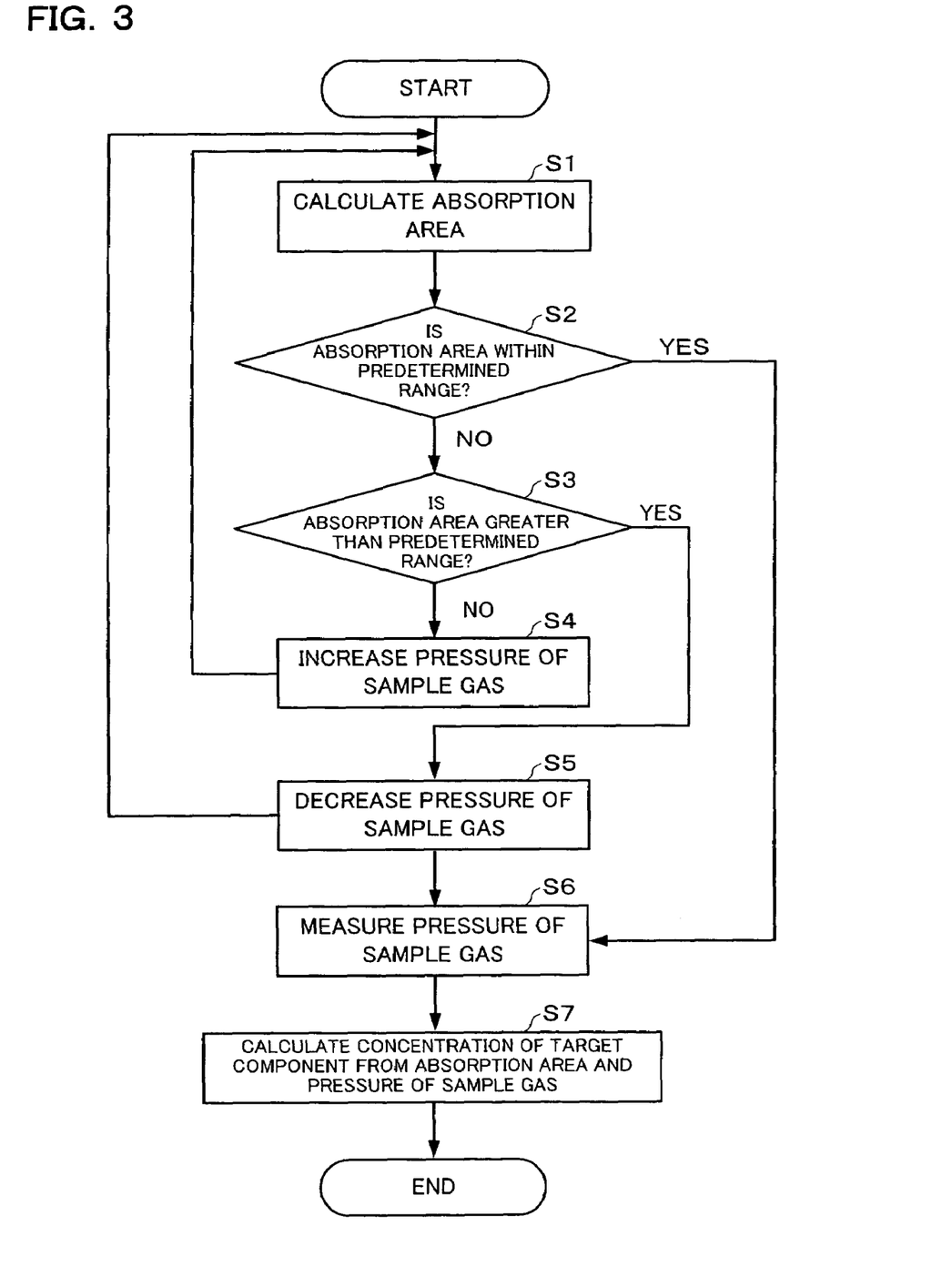
FIG. 3 is a flowchart schematically showing an infrared absorption measurement method according to the first embodiment of the present invention.
Figure 4:
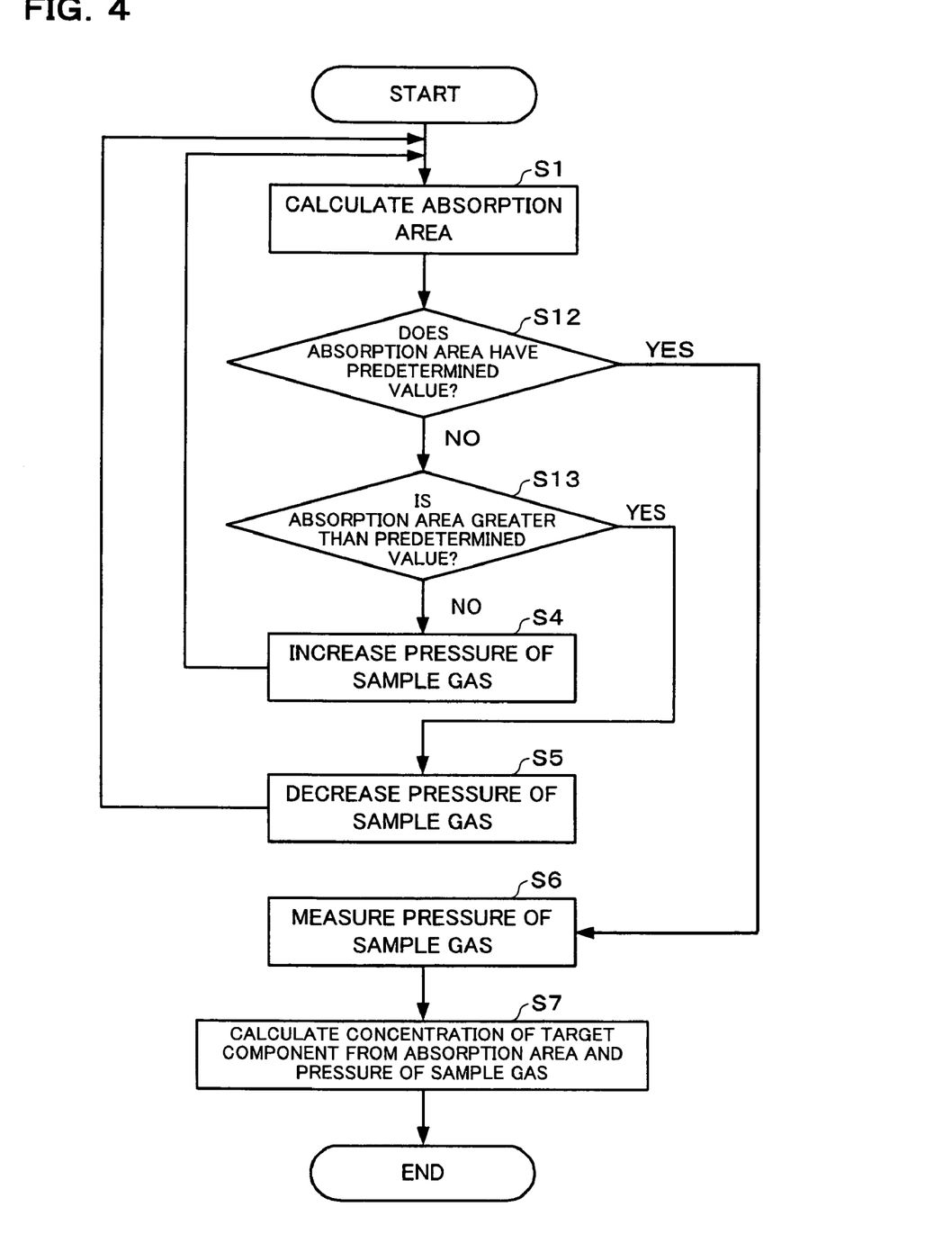
FIG. 4 is a flowchart schematically showing a modification of the infrared absorption measurement method according to the first embodiment.

FIG. 3 illustrates an example in which the pressure $P_2$ of the sample gas is adjusted so that the absorption area of the peak region which indicates the target component is within the predetermined range. However, as shown in FIG. 4, the pressure $P_2$ of the sample gas may be adjusted so that the absorption area of the peak region which indicates the target component has a predetermined value. FIG. 4 is a flowchart schematically showing a modification of this embodiment.

As shown in FIG. 4, the pressure $P_2$ of the sample gas is adjusted by using the feedback mechanism 33 so that the absorption area of the peak region which indicates the target component has a predetermined value (steps S12 and S13). In this case, the temporary concentration $M_1$ in the above equation (1) has a single value if the absorption area has the predetermined value. This enables the concentration $M_2$ of the sample gas to be calculated conveniently by using the concentration calculation section 35 from the pressure $P_1$ of the gas including the target component used to create the calibration curve during infrared absorption measurement and the pressure $P_2$ of the sample gas during decompression by referring to the above equation (1).

2. Second Embodiment

Figure 2:
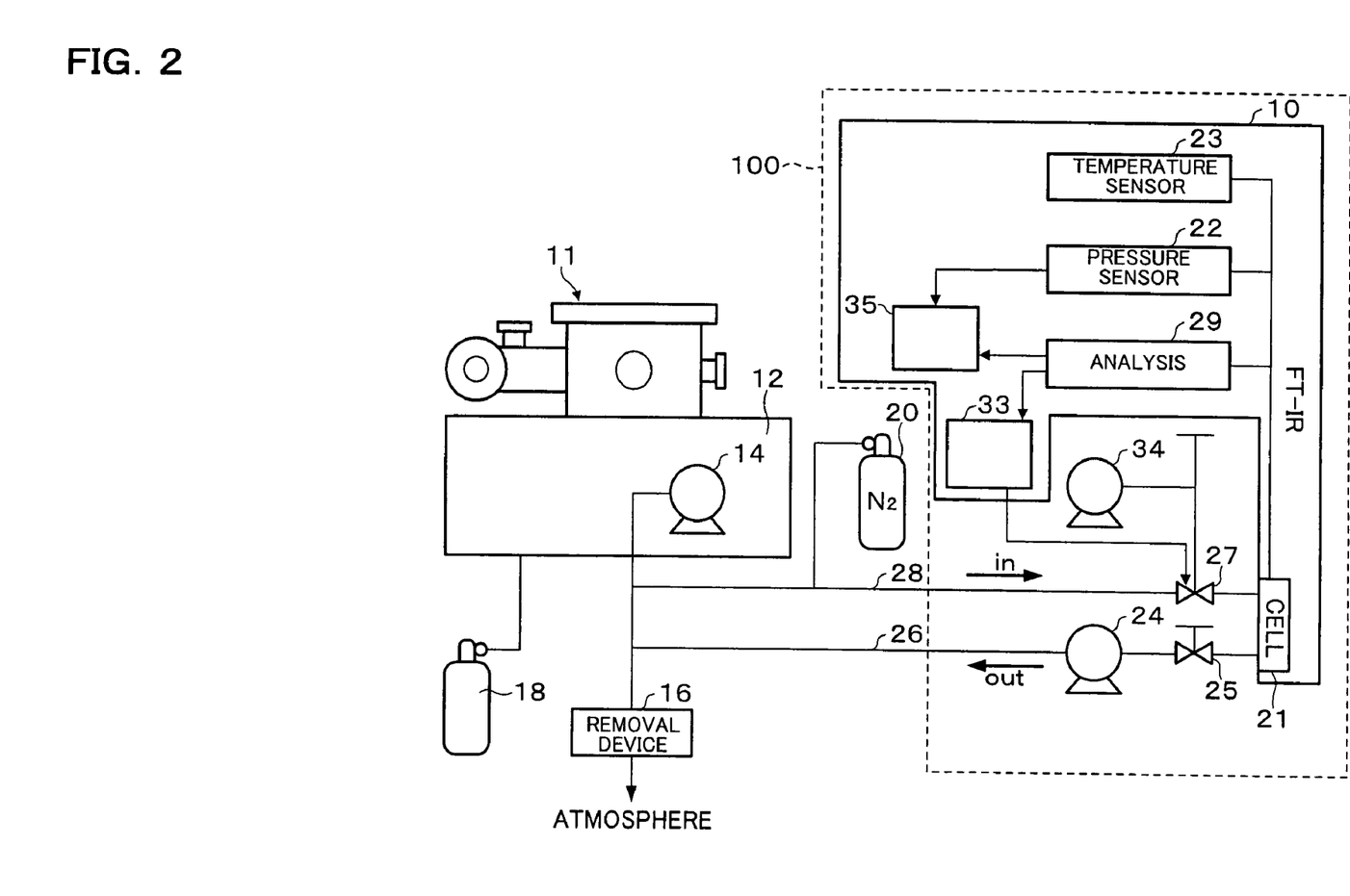
FIG. 2 is a diagram schematically showing an infrared absorption measurement device according to a second embodiment of the present invention.

FIG. 2 is a diagram schematically showing semiconductor manufacturing device 11 connected with the infrared absorption measurement device 100 in this embodiment. This embodiment illustrates the case where the infrared absorption measurement device 100 in the first embodiment is used to quantitatively analyze the target component included in the gas discharged from the semiconductor manufacturing device 11.

In the infrared absorption measurement device 100 in this embodiment, a gas discharged from the semiconductor manufacturing device 11 is mixed with nitrogen gas 20 to form a sample gas. The sample gas is introduced into the infrared absorption analysis device 10 through the gas inlet line 28, and infrared absorption of each target component included in the sample gas is measured by using the infrared absorption analysis device 10.

In the semiconductor manufacturing device 11, a semiconductor manufacturing process such as dry etching or chemical vapor deposition (CVD) is performed. In the dry etching step, perfluorocarbon (PFC) is used as gas plasma. This embodiment illustrates the case where $C_4F_8$ (PFC) is used as etching gas. However, the measurement target gas of the infrared absorption measurement device in this embodiment is not limited to $C_4F_8$.

PFC is one type of greenhouse gas. Greenhouse gases include $CO_2$, $NO_x$, and methane in addition to PFC. These greenhouse gases have a strong absorption in the infrared radiation region, and absorb energy radiated from the earth's surface when released to the atmosphere. The absorbed energy is released to space and the earth's surface. In this case, a part of the energy released from the earth's surface is returned thereto by the greenhouse gases, whereby the temperature of the earth's surface is increased. Greenhouse gases are considered to bring about greenhouse effects through this mechanism.

As an index for comparing the degree of greenhouse effects caused by greenhouse gases, a global warming potential (GWP) has been proposed. GWP indicates the greenhouse effects per unit weight of each gas relative to $CO_2$. PFC is a greenhouse gas having a particularly high greenhouse effect. PFC has an extremely high GWP). For example, the GWP of $CF_4$ is approximately 6500 times that Of $CO_2$. PFC is stable in comparison with other gases, and has an extremely long atmospheric lifetime. For example, the atmospheric lifetime of $CF_4$ is approximately 50,000 years. Therefore, PFC warms the earth for many years once it is released to the atmosphere.

PFC is generally used in the manufacturing steps of semiconductor devices, and is widely used in devices using low pressure plasma. In a dry etching system, PFC such as $CF_4$ or $C_4F_8$ is used to etch $SiO_2$ or $Si_3N_4$. In a CVD system, gas plasma such as $C_2F_6$ is generally used to clean a silicon compound film adhering to the system or the like. A PFC liquid is used as a solvent for cooling a wafer. However, since PFC has a high greenhouse effect as described above, reduction of emission of PFC has been demanded internationally.

In order to demonstrate the reduction of emission of PFC, it is necessary to measure PFC gases emitted from factories. Since it is difficult to actually measure PFC gases emitted from factories, PFC gases emitted from semiconductor manufacturing device using PFC is measured, and emission of PFC is determined from the ratio of the gas emitted to the gas used (emission factor) and the amount of gas consumed in factories. The emission factor is calculated by measuring PFC gas actually emitted from the semiconductor manufacturing device.

In the case of performing dry etching by using $C_4F_8$ in a chamber 12 of the semiconductor manufacturing device 11, $CF_4$, $CHF_3$, $C_2F_4$, $C_2F_6$, $C_3F_8$, $C_4F_8$, $C_5F_5$, $COF_2$, $HF$, $SiF_4$, $OF_2$, $NF_3$, $SO_2$, $SF_6$, $SO_2F_2$, $SOF_2$, $NO$, $N_2O$, $NO_2$, $CO$, and $CO_2$ may be included in the discharged gas depending on the composition of an insulating layer formed on a semiconductor substrate to be processed.

In the case of generating $C_4F_8$ gas plasma in order to perform dry etching in the chamber 12 of the semiconductor manufacturing device 11, after evacuating the atmosphere in the chamber 12 by using a pump, a predetermined amount of $C_4F_8$ is introduced into the chamber 12, and a high voltage is applied. This causes $C_4F_8$ gas plasma to be generated. This gas plasma is used for dry etching. In this case, a predetermined percentage of $C_4F_8$ used is decomposed into $CF_4$ and the like, and the remaining $C_4F_8$ is discharged as is from the chamber 12. The discharged gas is absorbed by using a pump 14, and optionally diluted with nitrogen gas supplied from the nitrogen gas cylinder 20 to obtain a sample gas. The sample gas is introduced into the infrared absorption analysis device 10, and infrared absorption of each target component in the sample gas is measured.

As shown in FIG. 1, the infrared absorption measurement device 100 includes the pump 34 for decompressing the sample gas. The pump 34 is provided in the middle of the gas inlet line 28 through the valve 27. The sample gas discharged from the semiconductor manufacturing device 11 is decompressed by using the pump 34, and introduced into the cell 21 in the infrared absorption analysis device 10. Therefore, infrared absorption is measured in the cell 21 in a state in which the sample gas is decompressed. In this case, the pressure of the sample gas may be adjusted by using the valve 27.

After the measurement, the sample gas is introduced into a removal device 16 from the cell 21 through the discharge line 26. After harmful substances in the sample gas are removed by using the removal device 16, the sample gas is released to the atmosphere.

According to this embodiment, effects the same as the effects of the infrared absorption measurement method and the infrared absorption measurement device 100 in the first embodiment are obtained. Moreover, according to this embodiment, each target component in the discharged gas produced in the manufacturing process of semiconductor devices can be analyzed with high accuracy. For example, the concentration of greenhouse gas such as PFC can be accurately measured.

Solid products produced during the manufacturing process are generally included in the gas discharged from the semiconductor manufacturing device. In the case where the semiconductor manufacturing process is etching of an insulating layer, solid products originating from the insulating layer produced by etching are included in the discharged gas. According to the infrared absorption measurement method in this embodiment, since infrared absorption is measured in the cell 21 in a state in which the sample gas is decompressed, the period of time in which the sample gas resides in the cell 21 is reduced in comparison with the case of measuring the sample gas under normal pressure. This prevents solid products from adhering to the cell 21.

This embodiment illustrates the case where the infrared absorption measurement device 100 is provided separately from the semiconductor manufacturing device 11. However, the infrared absorption measurement device 100 may be provided inside the semiconductor manufacturing device 11.

The present invention is not limited to the above-described embodiments. Various modifications and variations are possible. For example, the present invention includes configurations essentially the same as the configurations described in the embodiments (for example, configurations having the same function, method, and results, or configurations having the same object and results). The present invention includes configurations in which any unessential part of the configuration described in the embodiments is replaced. The present invention includes configurations having the same effects or achieving the same object as the configurations described in the embodiments. The present invention includes configurations in which conventional technology is added to the configurations described in the embodiments.

What is claimed is:

1. An infrared absorption measurement method comprising:
   (a) measuring infrared absorption of a target component in a sample gas while decompressing the sample gas so that an absorption area in a peak region of the target component in the infrared absorption shown in a graph is within a predetermined range, the graph showing the relationship between the wave number and absorbance of the sample gas; and
   (b) calculating the concentration of the target component in the sample gas based on the absorption area and pressure of the decompressed sample gas.

2. The infrared absorption measurement method as defined in claim 1, wherein:
   a temporary concentration $M_1$ corresponding to the absorption area is calculated in the step (b) by referring a calibration curve which represents the relationship between the concentration and absorption area of a reference gas including the target component; and
   when the pressure of the reference gas is $P_1$ and the pressure of the decompressed sample gas is $P_2$, a concentration $M_2$ of the sample gas is obtained by:

$$M_2 = M_1 P_1 / P_2.$$

3. The infrared absorption measurement method as defined in claim 1,
   wherein the sample gas is decompressed in the step (a) so that the absorption area has a predetermined value.

4. The infrared absorption measurement method as defined in claim 1, wherein:
   an infrared absorption region of the target component shown in the graph includes a main peak region and a sub-peak region; and
   the peak region is the main peak region.

5. The infrared absorption measurement method as defined in claim 1,
   wherein the target component is included in a gas discharged from a semiconductor manufacturing device.

6. A method of manufacturing a semiconductor device, comprising:
   calculating the concentration of the target component in the sample gas by using the infrared absorption measurement method as defined in claim 1,
   wherein the target component is included in a gas discharged from a semiconductor manufacturing device.

7. An infrared absorption measurement device comprising:
   a pump which decompresses a sample gas including a target component;
   an infrared absorption analysis device which measures infrared absorption of the target component in the sample gas decompressed by the pump; and
   a feedback mechanism which adjusts the pressure of the sample gas so that an absorption area in a peak region of the target component in the infrared absorption shown in a graph is within a predetermined range, the graph showing the relationship between the wave number and absorbance of the sample gas.

8. The infrared absorption measurement device as defined in claim 7,
   wherein the feedback mechanism adjusts the pressure of the sample gas so that the absorption area has a predetermined value.

9. The infrared absorption measurement device as defined in claim 7, wherein:
   the infrared absorption analysis device includes an analysis section which calculates the absorption area and transmits information on the absorption area to the feedback mechanism; and
   the feedback mechanism adjusts the pressure of the sample gas based on the transmitted information on the absorption area.

10. The infrared absorption measurement device as defined in claim 7, further comprising:
    a concentration calculation section which calculates the concentration of the target component in the sample gas based on the information on the absorption area and information on the pressure of the sample gas.

11. The infrared absorption measurement device as defined in claim 7, wherein:
    an infrared absorption region of the target component shown in the graph includes a main peak region and a sub-peak region; and
    the peak region is the main peak region.

* * * * *